(12) United States Patent
Reiher et al.

(10) Patent No.: US 6,177,552 B1
(45) Date of Patent: Jan. 23, 2001

(54) FIBER-REACTIVE AZO COMPOUNDS, PROCESSES FOR THEIR PREPARATION AND THEIR USE AS DYES

(75) Inventors: Uwe Reiher, Hofheim; Ron Pedemonte, Eppstein-Vockenhausen, both of (DE)

(73) Assignee: DyStarTextilfarben GmbH & Co. Deutschland KG (DE)

(\*) Notice: Under 35 U.S.C. 154(b), the term of this patent shall be extended for 0 days.

(21) Appl. No.: 09/473,890

(22) Filed: Dec. 28, 1999

(51) Int. Cl.[7] .................. C09B 62/507; C09B 62/085; D06P 1/38; C07C 317/32
(52) U.S. Cl. .................. 534/632; 534/635; 534/638; 534/642; 558/29; 564/341
(58) Field of Search .................... 534/642, 632, 534/635, 638; 564/341; 558/29

(56) References Cited

U.S. PATENT DOCUMENTS

| | | | |
|---|---|---|---|
| 2,784,204 | \* 3/1957 | Heyna et al. | 534/642 |
| 4,754,023 | 6/1988 | Tzikas et al. | 534/618 |

\* cited by examiner

Primary Examiner—Fiona T. Powers
(74) Attorney, Agent, or Firm—Connolly Bove Lodge & Hutz LLP

(57) ABSTRACT

Described are fiber-reactive water-soluble azo compounds which contain a group of the general formula (2)

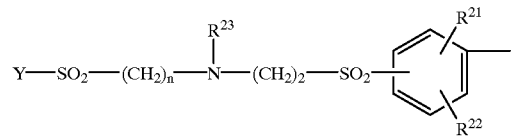

(2)

as diazo component where $R^{21}$ is hydrogen, methyl, ethyl, methoxy, ethoxy or sulfo, $R^{22}$ is hydrogen, methyl, ethyl, methoxy, ethoxy or sulfo, $R^{23}$ is hydrogen, alkyl of 1 to 4 carbon atoms or phenyl, n is 2 or 3 and the group —$SO_2$—Y is a fiber-reactive group of the vinyl sulfone series, and which are capable of dyeing hydroxy- and/or carboxamido-containing material, especially fiber material, such as cellulose fibers, for example cotton, or regenerated cellulose fibers and also wool and synthetic polyamide fibers in high color strength and good fastnesses.

22 Claims, No Drawings

FIBER-REACTIVE AZO COMPOUNDS, PROCESSES FOR THEIR PREPARATION AND THEIR USE AS DYES

The present invention is in the technical field of fiber-reactive azo dyes.

Azo compounds which possess a fiber-reactive group and have dye properties and can be used, for example, for dyeing cellulose fibers are known and extensively described in the literature, especially in patents and patent applications, for example in U.S. Pat. No. 4,754,023. However, these conventional azo dyes or, to be more precise, the dyeings obtainable therewith do not adequately meet the recent high expectations with regard to quality. More particularly, their fastness level and specifically the washoff of unfixed portions from the resulting dyeings leaves something to be desired with many of these dyes.

The present invention provides novel fiber-reactive azo compounds whose dyeings surprisingly meet these requirements.

The present invention accordingly relates to azo compounds, in particular monoazo, disazo and trisazo compounds, conforming to the general formula (1)

where

D is a group of the general formula (2)

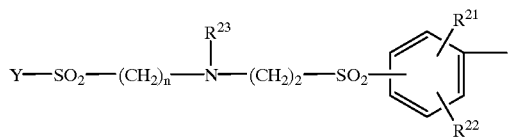

where:

$R^{21}$ is hydrogen, methyl, ethyl, methoxy, ethoxy or sulfo, preferably hydrogen, methyl, methoxy and sulfa and particularly preferably hydrogen;

$R^{22}$ is hydrogen, methyl, ethyl, methoxy, ethoxy or sulfa, preferably hydrogen or methoxy and particularly preferably hydrogen;

$R^{22}$ is hydrogen, alkyl of 1 to 4 carbon atoms, such as methyl and ethyl, or phenyl, preferably alkyl of 1 to 4 carbon atoms;

n is 2 or 3, preferably 2;

Y is vinyl or is a group of the general formula (3)

where Z is a substituent which is eliminable by alkali with the formation of a vinyl group;

the $SO_2$ grouping on the benzene nucleus is preferably meta and particularly preferably para to the amino group;

K is the radical of a sulfa- and/or carboxy-containing compound which possesses the function of a singly or doubly coupleable coupling component or contains the latter as a moiety attached to the azo group, the coupling component being selected -from the following compounds: aminobenzenes, diaminobenzenes and phenols, in particular their sulfonic acids and carboxylic acids; naphthols, in particular their sulfonic acids and carboxylic acids; aminonaphthols, in particular their sulfonic acids; acylaminonaphthols, in particular their sulfonic acids, with the acyl radical of an alkanecarboxylic acid having 1 to 4 carbon atoms in the alkyl radical, or of an alkenecarboxylic acid having 2 to 4 carbon atoms in the alkenyl radical, or of an aromatic carboxylic acid, such as of benzoic acid, or of an aromatic sulfanic acid, such as of benzene- or toluene-sulfonic acid, or of an N-substituted carbamic acid, such as of the N-phenylureido radical; dihydroxynaphthalenesulfonic acids; phenylazo- and naphthylazoaminonaphtholsulLonic acids; 5-pyrazolones and 5-aminopyrazoles; acetoacetylarylides; 2-hydroxy-6-pyridones; hydroxyquinolines; it also being possible for K to contain one or more fiber-reactive groups in addition to the substituents customary in water-soluble dyes, such as, for example, a group of the general formula —$SO_2$—Y where Y has one of the abovementioned meanings or a 2-chloro- or 2-fluoro-4-morpholino-1,3,5-triazin-6-ylamino group or a 2-fluoro- or 2-chloro-4-amino-1,3,5-triazin-6-ylamino group whose amino group in the 4-position can be mono- or disubstituted by alkyl of 1 to 4 carbon atoms and/or phenyl and the phenyl radical is unsubstituted or substituted by substituents from the group comprising sulfo, carboxy, methyl, ethyl, methoxy, ethoxy, chlorine, bromine and —$SO_2$—Y where Y has one of the abovementioned meanings.

Customary substituenis which may be present in the aromatic or heterocyclic radicals of K, as well as the aforementioned sulfo and carboxy groups, include for example substituents selected from the following group: alkyl of 1 to 4 carbon atoms, such as methyl, ethyl, propyl, isopropyl or butyl, of which preferably ethyl and particularly methyl; a koxy of 1 to 4 carbon atoms, such as methoxy, ethoxy, propoxy, isopropoxy and butoxy, of which preferably ethoxy and especially methoxy; alkanoylamino of 2 to 5 carbon atoms, such as acetylamino and propionylamino; benzoylamino; sulfo-, carboxy-, methyl-, ethyl-, methoxy-, ethoxy- and/or chlorine-substituted benzoylamino; amino; mono($C_1$–$C_4$-alkyl)amino, di($C_1$–$C_4$-alkyl)amino, phenylamino and N-($C_1$–$C_4$-alkyl)-N-phenylamino, whose alkyl groups may be substituted, for example by phenyl, sulfophenyl, hydroxy, sulfato, sulfo and carboxy, and whose phenyl groups may be substituted, as by chlorine, sulfo, carboxy, methyl and/or methoxy, for example methylamino, ethylamino, propylamino, isopropylamino, butylamino, N,N-di(β-hydroxyethyl)amino, N,N-di(βsulfatoethyl)amino, sulfobenzylamino, N,N-di(sulfobenzyl)amino, diethylamino, phenylamino and sulfophenylamino; alkoxycarbonyl of 2 to 5 carbon atoms, such as methoxycarbonyl and ethoxycarbonyl; alkylsulfonyl of 1 to 4 carbon atoms, such as methylsulfonyl and ethylsulfonyl; trifluoromethyl; nitro; cyano; ureido; hydroxy; sulfomethyl; halogen, such as fluorine, chlorine and bromine; carbamoyl which may be mono- and disubstituted by alkyl of 1 to 4 carbon atoms, N-phenylcarbamoyl and N-phenyl-N-($C_1$–$C_4$-alkyl) carbamoyl, whose alkyl groups may be substituted, for example by hydroxy, sulfato, sulfo, carboxy, phenyl and sulfophenyl, and whose phenyl groups may be substituted, for example by methyl, ethyl, methoxy, ethyl, sulfo, carboxy, chlorine and cyano, for example N-methylcarbamoyl and N-ethylcarbamoyl; N-sulfamoyl which may be mono- or disubstituted by alkyl of 1 to 4 carbon atoms, N-phenylsulfamoyl and N-phenyl-N-alkylsulfamoyl having alkyl of 1 to 4 carbon atoms, whose alkyl may be substituted, for example by hydroxy, sulfato, sulfo, carboxy, phenyl and sulfophenyl, and whose phenyl groups may be substituted, for example by methyl, ethyl, methoxy, ethyl, sulfo, carboxy, chlorine and cyano, for example N-methylsulfamoyl, N-ethylsulfamoyl, N-propylsulfamoyl, N-isopropylsulfamoyl, N-butylsulfamoyl, N-(β-hydroxy-ethyl)sulfamoyl and N,N-di-(β-hydroxyethyl)sulfamoyl.

Alkali-eliminable substituents Z are, for example, halogen atoms, such as the bromine atom and chlorine atom, ester groups of organic carboxylic and sulfonic acids, such as an alkanoyloxy group of 2 to 5 carbon atoms, for example the acetoxy group, or a sulfobenzoyloxy, benzoyloxy, phenylsulfonyloxy or toluylsulfonyloxy group, furthermore, for example, phosphate, sulfato and thiosulfato groups, similarly dialkylamino groups containing alkyl groups of 1 to 4 carbon atoms each, such as dimethylamino and diethylamino. Y is preferably a vinyl group and in particular a β-sulfatoethyl group.

Sulfo groups are groups of the general formula —SO$_3$M, carboxy groups are groups of the general formula —COOM, sulfato groups are groups of the general formula —OSO$_3$M, thiosulfato groups are groups of the general formula —S—SO$_3$M and phosphato groups are groups of the general formula —OPO$_3$M$_2$, in which M is a hydrogen atom or a salt-forming metal atom, such as, in particular, an alkali metal atom, such as, for example, sodium, potassium or lithium.

Of the compounds according to the invention of the general formula (1), for example, those compounds may be mentioned in particular in which K is a radical of the formula (4a), (4b) (4c) , (4d) , (4e) , (4f), (4g), (4h), (4i) (4k), (4m), (4n) (4p), (4q), (4r), (4s) and (4t) below:

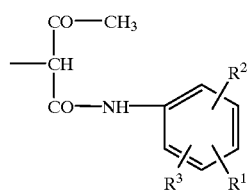
(4a)

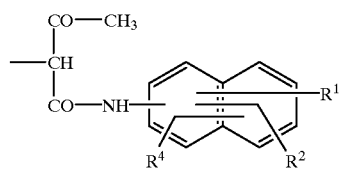
(4b)

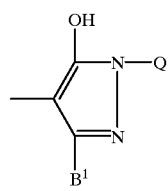
(4c)

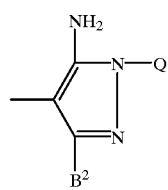
(4d)

-continued

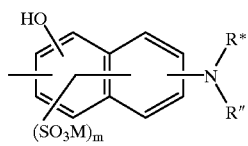
(4e)

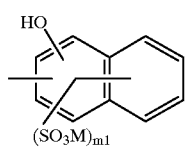
(4f)

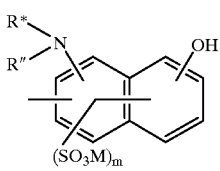
(4g)

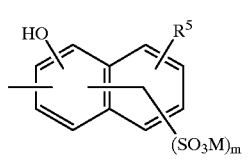
(4h)

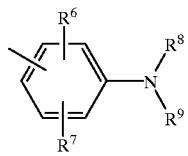
(4i)

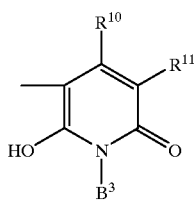
(4k)

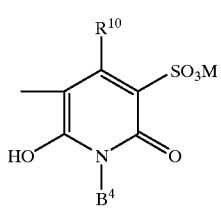
(4m)

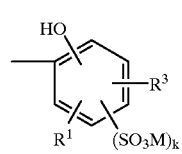
(4n)

-continued

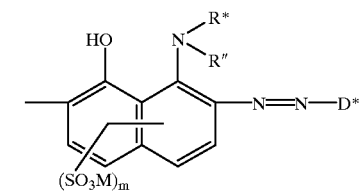
(4p)

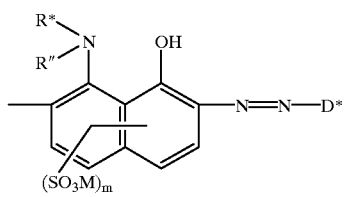
(4q)

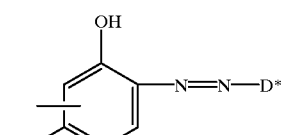
(4r)

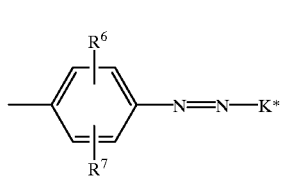
(4s)

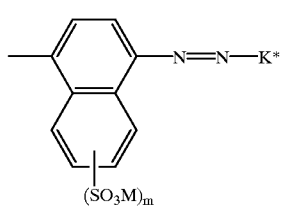
(4t)

In these formulae, the symbols have the following meanings:

$R^1$ is hydrogen, carboxy, sulfo or a group of the general formula —$SO_2$—Y where Y has the above meaning, or is a group of the general formula (a) or (b) or (c)

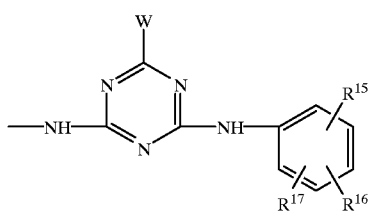
(a)

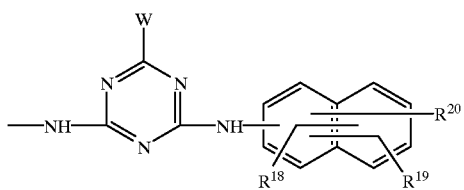
(b)

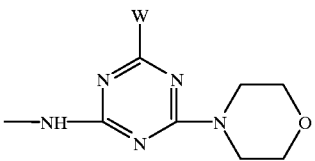
(c)

where $R^{15}$ is hydrogen, sulfo, carboxy or a group of the general formula —$SO_2$—Y where Y is as defined above, $R^{16}$ is hydrogen, alkyl of 1 to 4 carbon atoms, such as methyl and ethyl, alkoxy of 1 to 4 carbon atoms, such as methoxy and ethoxy, chlorine, bromine, carboxy, sulfo or nitro, preferably hydrogen, methoxy, ethoxy, methyl, ethyl, sulfo or carboxy, $R^{17}$ is hydrogen, alkyl of 1 to 4 carbon atoms, such as methyl and ethyl, alkoxy of 1 to 4 carbon atoms, such as methoxy and ethoxy, chlorine or bromine, preferably hydrogen, methoxy or ethoxy, $R^{18}$ is hydrogen, sulfo, carboxy or a group of the general formula —$SO_2$—Y where Y is as defined above and is preferably hydrogen, sulfo or a group of the general formula —$SO_2$—Y where Y is as defined above, $R^{19}$ is hydrogen or sulfo, $R^{20}$ is hydrogen or sulfo, and W is fluorine or chlorine;

$R^2$ is hydrogen, alkyl of 1 to 4 carbon atoms, such as methyl and ethyl, alkoxy of 1 to 4 carbon atoms, such as methoxy and ethoxy, chlorine, bromine, carboxy, sulfo or nitro, preferably hydrogen, methoxy, ethoxy, methyl, ethyl, sulfo or carboxy;

$R^3$ is hydrogen, alkyl of 1 to 4 carbon atoms, such as methyl and ethyl, alkoxy of 1 to 4 carbon atoms, such as methoxy and ethoxy, chlorine or bromine, preferably hydrogen, methoxy or ethoxy;

$R^4$ is hydrogen, sulfo or carboxy, preferably hydrogen or sulfo, and in particular is hydrogen in the case where $R^1$ is a group of the formula —$SO_2$—Y where Y has the abovementioned meaning or a group of the abovementioned and defined general formula (a), (b) or (c);

$B^1$ is alkyl of 1 to 4 carbon atoms, such as methyl, carboxy, carbalkoxy of 2 to 5 carbon atoms, such as carbomethoxy and carbethoxy, carbamoyl, phenyl or phenyl substituted by sulfo, carboxy, methyl, ethyl, methoxy, ethoxy and/or chlorine;

$B^2$ is alkyl of 1 to 4 carbon atoms, such as methyl, carboxy, carbalkoxy of 2 to 5 carbon atoms, such as carbomethoxy and carbethoxy, carbamoyl, phenyl or phenyl substituted by 1 or 2 substituents from the group comprising alkyl of 1 to 4 carbon atoms, alkoxy of 1 to 4 carbon atoms, chlorine, bromine and sulfo;

Q is phenyl, which can be substituted, such as, for example, by 1, 2 or 3, preferably 1 or 2, substituents from the group comprising chlorine, bromine, methyl, ethyl, methoxy, ethoxy, carboxy, sulfo and alkanoylamino of 2 to 5 carbon atoms, such as acetylamino, and/or by a group of the general formula —$SO_2$—Y where Y has the abovementioned meaning, or is naphthyl, which can be mono-, di- or tri-substituted by sulfo and, if desired, by 1 alkyl of 1 to 4 carbon atoms, 1 alkoxy of 1 to 4 carbon atoms, 1 chlorine or 1 alkanoylamino of 2 to 5 carbon atoms and/or by a group of the general formula —SO$_2$—Y where Y has the abovementioned meaning;

R* is hydrogen or alkyl of 1 to 4 carbon atoms, which can be substituted by phenyl or by phenyl which is substituted by sulfo and/or —SO$_2$—Y where Y has the above meaning;

R" is hydrogen or alkyl of 1 to 4 carbon atoms, which can be substituted by phenyl, sulfophenyl or a group of the formula —SO$_2$—Y where Y has the above meaning, or is phenyl or phenyl substituted by 1 or 2 substituents from the group comprising alkyl of 1 to 4 carbon atoms, alkoxy of 1 to 4 carbon atoms, chlorine, bromine, sulfo and —SO$_2$—Y where Y has the above meaning;

$R^5$ is phenylureido, the phenyl radical of which can be substituted by a group of the formula —SO$_2$—Y where Y has the above meaning, or is alkanoylamino of 2 to 5 carbon atoms, such as acetylamino or propionylamino, which can be substituted in the alkyl radical by a group of the formula —SO$_2$—Y where Y has the above meaning, or is alkenoylamino of 3 to 5 carbon atoms, such as acryloylamino, or is benzoylamino, which can be substituted by substituents from the group comprising chlorine, methyl, methoxy, nitro, sulfo, carboxy and —SO$_2$—Y where Y has the above meaning, and is preferably acetylamino or benzoylamino;

$R^6$ is hydrogen, alkyl of 1 to 4 carbon atoms, alkoxy of 1 to 4 carbon atoms, sulfo, carboxy, carbalkoxy of 2 to 5 carbon atoms, such as carbomethoxy and carbethoxy, halogen, such as bromine or chlorine, or alkoxy of 1 to 4 carbon atoms which is substituted by hydroxy, acetyloxy, carboxy, carbamoyl, cyano or halogen, such as chlorine;

$R^7$ is hydrogen, alkyl of 1 to 4 carbon atoms, alkoxy of 1 to 4 carbon atoms, halogen, such as bromine or chlorine, cyano, trifluoromethyl, alkoxy of 1 to 4 carbon atoms which is substituted by hydroxy, acetyloxy, carboxy, carbamoyl or cyano or halogen, such as chlorine, or by a group of the formula —SO$_2$—Y where Y has the above meaning, or is alkanoylamrino of 2 to 5 carbon atoms, which can be substituted by chlorine, bromine, alkoxy of 1 to 4 carbon atoms, phenoxy, phenyl, hydroxy, carboxy or sulfo or a group of the formula —SO$_2$—Y where Y has the above meaning, or is alkenoylamino of 3 to 5 carbon atoms, which can be substituted by chlorine, bromine, carboxy or sulfo, or is benzoylamino, which can be substituted in the benzene ring, for example by substituents from the group comprising chlorine, methyl, sulfo and a group of the formula —SO$_2$—Y where Y has the above meaning, or is alkylsulfonyl of 1 to 4 carbon atoms or phenylsulfonyl, which can be substituted in the benzene ring, for example by substituents from the group comprising chlorine, methyl, sulfo and a group of the formula —SO$_2$—Y where Y has the above meaning, or is alkylsulfonylamino of 1 to 4 carbon atoms, which can be substituted by hydroxy, sulfato, chlorine, bromine, alkoxy of 1 to 4 carbon atoms or a group of the formula —SO$_2$—Y where Y has the above meaning, or is phenylsulfonylamino, which can be substituted in the benzene ring, for example by substituents from the group comprising chlorine, methyl, sulfo and a group of the formula —SO$_2$—Y where Y has the above meaning, or is carbamoyl, which can be mono- or disubstituted on the nitrogen atom by 1 or 2 substituents selected from the group of subs-ituents consisting of alkyl of 1 to 4 carbon atoms, alkyl of 1 to 4 carbon atoms which is substituted, for example, by hydroxy, sulfo, carboxy, sulfato or phenyl or a group of the formula —SO$_2$—Y where Y has the above meaning, cycloalkyl of 5 to 8 carbon atoms, phenyl and phenyl which is substituted by substituenrs, for example from the group comprising chlorine, sulfo, methyl, methoxy, carboxy and a group of the formula —SO$_2$—Y where Y has the above meaning, or is sulfamoyl, which can be mono- or disubstituted on the nitrogen atom by 1 or 2 subsrituents selected from the group of substituents consisting of alkyl of 1 to 4 carbon atoms, alkyl of 1 to 4 carbon atoms which is substituted by substituents, for example from the group comprising hydroxy, sulfo, carboxy, sulfato or phenyl or a group of the formula —SO$_2$—Y where Y has the above meaning, cycloalkyl of 5 to 8 carbon atoms, phenyl and phenyl which is substituted by substituents, for example from the group comprising chlorine, sulfo, methyl, methoxy, carboxy and a group of the formula —SO$_2$—Y where Y has the above meaning, or is ureido or ureido which can be mono- or disubstituted on the terminal nitrogen atom by 1 or 2 substituents selected from the group of substituents consisting of alkyl of 1 to 4 carbon atoms, alkyl of 1 to 4 carbon atoms which is substituted, for example, by hydroxy, sulfo, carboxy, sulfate, phenyl or a group of the formula —SO$_2$—Y where Y has the above meaning, cycloalkyl of 5 to 8 carbon atoms, phenyl and phenyl which is substituted by substituents, for example from the group comprising chlorine, sulfo, methyl, methoxy, carboxy and a group of the formula —SO$_2$—Y where Y has the above meaning;

$R^8$ is hydrogen or alkyl of 1 to 4 carbon atoms, which can be substituted, for example, by hydroxy, sulfo, carboxy, sulfatc, a group —SO$_2$—Y where Y has the above meaning, phenyl or sulfophenyl, or is alkenyl of 2 to 4 carbon atoms, which can be substituted by carboxy, sulfo, chlorine or bromine, or is cycloalkyl of 5 to 8 carbon atoms;

$R^9$ is hydrogen or alkyl of 1 to 4 carbon atoms, which can be substituted, for example by hydroxy, sulfo, carboxy, sulfate, phenyl or —SO$_2$—Y where Y has the above meaning, or is alkenyl of 2 to 5 carbon atoms, which can be substituted by carboxy, sulfo or —SO$_2$—Y where Y has the above meaning or by chlorine or bromine, or $R^9$ is cycloalkyl of 5 to 8 carbon atoms or phenyl, which can be substituted, for example by substituents selected from the group consisting of chlorine, sulfo, methyl, methoxy, carboxy and —SO$_2$—Y where Y has the above meaning, or $R^8$ and $R^9$ together with the nitrogen atom and optionally with a further heteroatom or a hetero group, such as N, O, S and NH, represent a 5- to 8-membered, preferably saturated, heterocyclic radical, such as, for example, the N-piperidino, N-morpholino or N-piperazino group;

$R^{10}$ is hydrogen or alkyl of 1 to 4 carbon atoms or alkyl of 1 to 4 carbon atoms which is substituted by alkoxy of 1 to 4 carbon atoms or cyano;

$R^{11}$ is hydrogen, sulfo, sulfoalkyl having an alkyl group of 1 to 4 carbon atoms, such as sulfomethyl, cyano or carbamoyl;

$B^3$ is hydrogen or alkyl of 1 to 6 carbon atoms, preferably of 1 to 4 carbon atoms, which can be substituted by phenyl, sulfo, sulfophenyl or —SO₂—Y where Y has the above meaning;

B⁴ is hydrogen, alkyl of 1 to 4 carbon atoms or alkyl of 1 to 4 carbon atoms which is substituted by alkoxy of 1 to 4 carbon atoms, such as methoxy, sulfo, carboxy, sulfato, acetylamino, benzoylamino or cyano or by a group of the formula —SO₂—Y where Y has the above meaning, or is alkenyl of 2 to 4 carbon atoms, cyclohexyl, phenyl or phenyl which is substituted by substituents selected from the group consisting of carboxy, sulfo, benzoylamino, acetylamino, —SO₂—Y where Y has the above meaning and chlorine;

k is the number zero or 1 (where, in the case where k is zero, this group is hydrogen);

m is the number 1 or 2;

m₁ is the number 1, 2 or 3;

D* is a group of the general formula (2) or is phenyl, which can be substituted by 1, 2 or 3, preferably 1 or 2, substituents selected from the group consisting of alkyl of 1 to 4 carbon atoms, alkoxy of 1 to 4 carbon atoms, chlorine, bromine, hydroxy, carboxy, sulfo, carbamoyl, sulfamoyl and alkanoylamino of 2 to 5 carbon atoms, of these, preferably methyl, methoxy, ethoxy, chlorine, sulfo, carboxy and hydroxy, and/or by a group of the formula —SO₂—Y where Y has the abovementioned meaning, one of these substituents being preferably a sulfo or carboxy group and the group —SO₂—Y being preferably in the meta- or para-position relative to the azo group, or D* is naphthyl which is substituted by 1, 2 or 3 sulfo groups or by 1 or 2 sulfo groups and 1 or 2 groups of the general formula —SO₂—Y where Y has the abovementioned meaning or only by one such group —SO₂—Y, it being possible for D and D* to have meanings which are identical to or different from one another;

K* is a radical of one of the general formulae (4a) to (4m) mentioned and defined above, it being possible for K and K* to have meanings which are identical to or different from one another;

M has one of the abovementioned meanings.

The individual formula members, including the formula members which may occur twice in the same formula, can, within the scope of their meaning, have meanings which are identical to or different from one another.

The free bonds present in the above formulae (4e), (4f), (4g), (4h), (4i) and (4n) and leading to the azo group, and the azo group in formula (4p) and (4q) are bound in the ortho-posizion relative to the hydroxy or amino group. This hydroxy group is preferably bound to the naphthalene radical in the α-position.

Alkyl groups of 1 to 4 carbon atoms are preferably the ethyl and in particular the methyl group; alkoxy groups of 1 to 4 carbon atoms are preferably the ethoxy and in particular the methoxy group; alkanoylamino groups of 2 to 5 carbon atoms are preferably the propionylamino group and in particular the acetylamino group, and carbalkoxy groups of 2 to 5 carbon atoms are preferably the carbomethoxy and carbethoxy groups.

Of the compounds according to the invention of the general formula (1), in particular those are preferred in which K is a radical of the general formula (4c), (4f), (4h), (4p) or (⁴q), in which in turn the individual formula members have the following preferred meanings:

B¹ is carboxy or methyl;

Q is phenyl, which can be substituted by 1 or 2 substituents which are selected from the following group of substituents: 2 methyl, 2 methoxy, 1 chlorine or bromine, 2 sulfo, 1 carboxy and 1 vinylsulfonyl or β-sulfatoethylsulfonyl;

R⁵ is acetylamino, propionylamino or benzoylamino, which can be substituted by 1 or 2 substituents from the group comprising chlorine, methyl, methoxy, nitro, sulfo and β-sulfatoethylsulfonyl;

R* and R" are both hydrogen;

m in formula (4p) and (4q) is the number 2, and the one group —SO₃M is in the meta position relative to the hydroxy group and the other group —SO₃M in the meta or para position to the amino group.

Particular preference is given to those compounds of the general formula (1) in which K is 1-hydroxy-2-naphthyi which is substituted by 1, 2 or 3 sulfo groups or a group of the general formula (4c) in which B¹ is carboxy or methyl and Q is phenyl which is substituted by 1 or 2 substituents selected from the group comprising 2 methyl groups, 2 ethoxy groups, 2 methoxy groups, 2 sulfo groups, 1 carboxy group or 1 chlorine atom, in which one of the substituents must be a carboxy or sulfo group, or the phenyl group is substituted by a vinylsulfonyl or β-sulfatoethylsulfonyl group and can additionally be substituted by 1 or 2 substituents selected from the group comprising 1 methyl, 2 methoxy, 1 chlorine and 1 sulfo.

The oresent invention furthermore relates to processes for the preparation of the azo compounds according to the invention of the general formula (1), for example by reaction (coupling reaction) of the diazonium compound of an amino compound of the general formula (5)

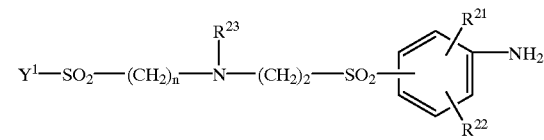

(5)

in which Y¹ has one of the meanings of Y or is the β-hydroxyethyl group, R²¹, R²², R²³ and n have the abovementioned meanings and the SO₂ on the benzene nucleus is preferably meta- and particularly preferably para- to the amino group, with a compound of the general formula H—K where K has the abovementioned meaning; if K, as mentioned above, is a divalent coupling component, a disazo compound if desired can be prepared by reaction of this divalent coupling component with a two-fold equimolar amount of the diazo component. In the case where a compound (5) in which yl is a β-hydroxyethyl group is used, this β-hydroxyethyl group in the resulting azo compound is converted into a group Y of the azo compound (1) according to the invention, as will be described later.

The diazotization and coupling reactions are carried out in the usual and long-known manner, for example the diazotization of the amine (5), as a rule, at a temperature between −5° C. and +15° C. and a pH below 2 by means of a strong acid and alkali metal nitrite in, preferably, aqueous medium, and the coupling reaction, as a rule, at a pH between 1.5 and 4.5 in the case of an amino-containing coupling component and at a pH between 3 and 7.5 in the case of a hydroxy-containing coupling component and at a temperature between 0 and 30° C. in, preferably, aqueous medium.

If the coupling component is a divalent, di-coupleable compound, it contains, for example, a coupleable amino group and, at the same time, a coupleable hydroxy group, a disazo compound can be prepared by carrying out the coupling reaction first with the first mole of the diazonium compound of the amine in a strongly acidic pH range to form the monoazo compound and the second coupling reaction with the second mole of the diazonium compound of the amine subsequently in a weakly acidic to weakly alkaline range. This procedure applies, for example, to the compounds in which K is a group of the general formula (4p) or (4q), for example by coupling the aminonaphtholsulfonic acid first with the first mole of the diazonium compound of the amine of the general formula (5) or any other aromatic amine of the general formula $D^*$—$NH_2$ where $D^*$ has the abovementioned meaning different from D, in a strongly acidic medium and then by coupling the resulting monoazo compound with the second mole of a diazonium compound of an amine $D^*$—$NH_2$ where $D^*$ has the abovementioned meaning in a weakly acidic, neutral or weakly alkaline range, it being necessary for $D^*$ to have one of the meanings given for D if the first coupling reaction was not carried out using a diazonium compound of an amine (5); for example, the coupling reactions are carried out in particular first at a pH of about 1 to 2.5 and then at a pH between 4 and 6.5, in which, if the diazonium compound of the amino compound (5) in both coupling reactions is identical, it is possible to carry out the first and second coupling reaction in one and the same batch, first in the strongly acidic range mentioned and then in a weakly acidic to weakly alkaline range. To prepare a disazo compound in which K is a group of the general formula (4r), the reaction of the coupling component resorclnol with the diazonium compound(s) is advantageously first carried out at a pH of between 0.8 and 2 and then at a pH between 6 and 7.5.

Disazo compounds of the general formula (1) whose radical K corresponds to the radical of an azo compound composed of a coupleable diazo component and a coupling component, such as, for example, a radical of the general formula (4s) or (4t), can also be prepared according to the invention by first coupling the diazonium compound of an amine (5) with the amino-containing and thus diazotizable coupling component, such as, for example, an aniline containing the substituents $R^6$ and $R^7$, or a sulfo-substituted 1-amino-naphthalene, and diazotizing the amino group in the aminoazo compound thus formed and coupling it with a coupling component, such as, for example, the coupling component H—$K^*$, to give the disazo compound.

All these possible reactions for synthesizing disazo compounds are analogous to the methods known in the literature or known to one skilled in the art for the synthesis of disazo compounds.

Examples of coupling components which can be used for the preparation of the dyes according to the invention and have, for example, the general formulae (4a) to (4n) are: 1,3-diamino-benzene-5-sulfonic acid, phenol, cresol, resorcinol, 2-ethoxyphenol, 4-methylphenol, 3-sulfophenol, sal-cylic acid, 3-sulfo-1-naphthol, 4-sulfo-1-naphthol, 5-sulfo-1-naphthol, 3,6-disulfo-8-naphthol, 4,6-disulfo-8-naphthol, 1-naphthol-3,8-disulfonic acid, 1-amino-8-naphthol-4-sulfonic acid, 1-amino-8-naphthol-5-sulfonic acid, 1-amino-8-naphthol-2,4-disulfonic acid, 2-amino-5-naphthol-7-sulfonic acid, 2-amino-5-naphthol-1,7-disulfonic acid, 1-amino-5-naphthol-7-sulfonic acid, 2-amino-8-naphthol-6-sulfonic acid, 2-amino-8-naphthol-3,6-disulfonic acid, 2-amino-8-naphthol-4,6-disulfonic acid, 1-amino-8-naphthol-3,6- or -4,6-disulfonic acid, 1-acryloylamino-8-naphthol-3,6- or -4,6-disulfonic acid, 1-propionylamino-8-naphthol-3,6- or -4,6-disulfonic acid, 1-acetylamino-8-naphthol-4-sulfonic acid, 1-acetylamino-8-naphthol-3,6- or -4,6-disulfonic acid, 1-benzoylamino-8-naphthol-3,6- or -4,6-disulfonic acid, 2-naphthol-5,7-disulfonic acid, 2-naphthol-3,6- and -6,8-disulfonic acid, 1,8-dihydroxynaphthalene-3,6-disulfonic acid, 1,8-dihydroxynaphthalene-6-sulfonic acid, 1-naphthol-3,6,8-trisulfonic acid, 2-acetylamino-5-naphthol-7-sulfonic acid, 2-benzoylamino-8-naphthol-6-sulfonic acid, 2-('-tosylamino)-5-naphthol-7-sulfonic acid, 2-acetylamino-8-naphthol-3,6-disulfonic acid, 2-acetylamino-5-naphthol-1,7-disulfonic acid, 3-benzoylamino-8-naphthol-6-sulfonic acid, 2-phenylsulfonylamino-5-naphthol-7-sulfonic acid, 2-(N-methyl-N-acetyl)amino-8-naphthol-6-sulfonic acid, N-ethyl-N-benzylaniline-3-sulfonic acid, N,N-bis-(β-hydroxyethyl)aniline, N,N-bis-(β-sulfatoethyl)aniline, N,N-bis-(β-hydroxyethyl)-2-methoxy-5-chloroaniline, N-(β-sulfatoethyl)-2,5-dimethoxyaniline, N-(β-sulfatoethyl)-2-chloroaniline, acetoacetyl-2-naph-hylamide-5-sulfonic acid, N-acetoacetylaniline-3- or -4-sulfonic acid, N-acetoacetyl-2-methoxy-5-sulfoaniline, N-acetoacetyl-4-methoxy-3-sulfoaniline, N-acetoacetyl-2-methoxy-5-methyl-4-sulfoaniline, N-acetoacetyl-2,5-dimethoxy-4-sulfoaniline, N-acetoacetyl-2-methoxy-5-methyl-4-(β-sulfatoethylsulfonyl)aniline, N-acetoacetyl-2,5-dimethoxy-4-(β-sulfatoethylsulfonyl)aniline, N-acetoacetyl-2-methoxy-5-(β-sulfatoethylsulfonyl)aniline, N-acetoacetyl-4-(β-sulfatoethylsulfonyl)aniline, N-acetoacetyl-3-(β-sulfatoethyl-sulfonyl)aniline, 1-(4'-β-sulfatoethylsulfonylphenyl)-3-methyl-5-pyrazolone, 1-(4'-β-sulfatoethylsulfonylphenyl)-3-carboxy-5-pyrazolone, !-(4'-sulfophenyl)-3-methyl-5-pyrazolone, 1-(4'-sulfophenyl)-3-carboxy-5-pyrazolone, 1-(2'-chloro-5'-sulfophenyl)-3-methyl- or -3-carboxy-5-pyrazolone, 1-(3'-sulfophenyl)-3-carboxy-5-pyrazolone, 1-(2'-methoxy-4'-sulfophenyl)-3-carboxy-5-pyrazolone, 1-(3'-sulfophenyl)-3-methyl-5-aminopyrazole, 1-(4'-sulfophenyl)-3-methyl-5-aminopyrazole, 1-(2'-methoxy-5'-sulfophenyl)-3-methyl-5-aminopyrazole, 1-(2'-methoxy-5'-methyl-4'-sulfophenyl)-3-methyl- 5-aminopyrazole, 1-(2'-chloro-5'-sulfophenyl)-3-meethyl-5-aminopyrazole, 1-(3'-amino-4'-siulfophenyl)-3-carbethoxy-5-pyrazolone, 1-(4'-β-sulfatoethylsulfonylphenyl)-3-carbethoxy-5-pyrazolone, 1-(3'-amino-6'-methylphenyl)-3-carboxy-5-pyrazolone, 2-N-methylamino-8-naphthol-6-sulfonic acid, 3-carboxy-5-pyrazolone, 1-phenyl-3-carboxy-5-pyrazolone, 1-(4'-nitrophenyl)-3-carboxy-5-pyrazolone, 1-(3'-acetylaminophenyl)-3-carboxy-5-pyrazolone, 1-(3'-carboxyphenyl)-3-methyl-5-pyrazolone, 2-hydroxy-3-carboxynaphthalene, 2-hydroxy-6-carboxynaphthalene, 8-hydroxyquinoline-5-sulfonic acid, 1,4-dimethyl-2-hydroxy-6-pyridone-5-sulfonic acid, N-sulfomethylaniline, 3-acetylamino-5-naphthol-7-sulfonic acid, 2-methylamino-8-naphthol-6-sulfonic acid, 2,5-disulfodiphenylamine, 4-sulfodiphenylamine, 1-[4'-chloro-6'-(4"β-sulfatoethylsulfonylphenyl)amino-1',3',5'-triazin-2'-yl]amino-8-naphthol-3,6-disulfonic acid, 1-[4'-chloro-6'-(4"-β-sulfatoethylsulfonylphenyl)amino-1',3',5'-triazin-2'-yl]amino-8-naphthol-4,6-disulfonic acid, 2-[4'-chloro-6'-(4"-β-sulfatoethylsulfonylphenyl)amino-1',3',5'-triazin-2'-yl]amino-8-naphthol-6-sulfonic acid, 3-[4'-chloro-6'-(4"-β-sulfatoethylsulfonylphenyl)amino-1',3',5'-triazin-2'-yl]amino-8-naphthol-3,6-disulfonic acid, 1-(4'-chloro-6'-methoxy-1',3',5'-triazin-2'-yl)amino-8-naphthol-3,6-disulfonic acid, 1-[4'-chloro-6'-methoxy-1',3',5¹--uriazin-2'-yl)amino-8-naphthol-4,6-disulfonic acid, 2-(4'-chloro-6'-methoxy-1',3',5'-triazin-2'-yl)amino-8-naphthol-6-sulfonic acid, 3-(4'-chloro-6'-methoxy-1',3',5'-triazin-2'-yl)amino-8-naphthol-6-sulfonic acid, 1-[4'-fluoro-6'-(4"-β- sulfatoethylsulfonylphenyl)amino-1',3',5'-triazin-2'-yl]amino-8-naphthol-3,6-disulfonic acid, 1-[4'-fluoro-6'-(4"-β-sulfatoethylsulfonylphenyl)amino-1',3',5'-triazin-2'-yl]amino-8-naphthol-4,6-disulfonic acid, 2-[4'-fluoro-6'-(4"-β-sulfatoethylsulfonylphenyl)amino-1',3',5'-triazin-2'-yl]amino-8-naphthol-6-sulfonic acid, 3-[4'-fluoro-6'-(4"-β-sulfatoethylsulfonylphenyl)amino-1',3',5'-triazin-2'-yl]amino-8-naphthol-6-sulfonic acid, 1-(4'-β-sulfatoethylsulfonylbenzoyl)amino-8-naphthol-3,6-disulfonic acid or -4,6-disulfonic acid, 2- or 3-(4'-β-sulfatoethylsulfonylbenzoyl)amino-8-naphthol-6-sulfonic acid, 1-{4'-chloro-6'-[β-(4"-β"-sulfatoethylsulfonylphenyl)ethyl]-1',3',5'-triazin-2'-yl}amino-8-naphthol-3,6- or -4,6-disulfonic acid, 1-{4'-chloro-6'-[β-(3"-β"-sulfatoethylsulfonylphenyl)-ethyl]-1',3',5'-triazin-2'-yl}amino-8-naphthol-3,6- or -4,6-disulfonic acid, 1-{4'-chloro-6'-[β-(4"-sulfophenyl)ethyl]-1',3',5'-triazin-2'-yl}amino-8-naphthol-3,6- or -4,6-disulfonic acid, 1-{4'-chloro-6'-{β-(2"5"-disulfophenyl)ethyl]-1',3', 5'-triazin-2'-yl}amino-8-naphthol-3,6- or -4,6-disulfonic acid, 1-{4'-fluoro-6'-[β-(3"55"-disulfophanyl)ethyl]-1',3',5'-triazin-2'-yl}amino-8-naphthol-3,6- or -4,6-disulfonic acid, 1-(β-hydroxyethyl)-4-methyl-6-hydroxy-2-pyridone, 1-(β-hydroxyethyl)-3-cyano-4-methyl-6-hydroxy-2-pyridone, 1-(β-hydroxyethyl)-3-carbamoyl-4-methyl-6-hydroxy-2-pyridone, 1-(β-hydroxyethyl)-4-methyl-6-hydroxy-2-pyridone-3-sulfonic acid, 1-(β-sulfatoethyl)-4-methyl-6-hydroxy-2-pyridone, 1-(β-sulfatoethyl)-3-cyano-4-methyl-6-hydroxy-2-pyridone, 1-(β-sulfatoethyl)-3-carbamoyl-4-methyl-6-hydroxy-2-pyridone, 1-(β-sulfatoethyl)-4-methyl-6-hydrcxy-2-pyridone-3-sulfonic acid, 1-(β-sulfatoethyl)-4-methyl-6-hydroxy-2-pyridone, 1-(β-sulfatoeLhyl)-3-carbamoyl-4-methyl-6-hydroxy-2-pyridone, 1-(β-sulfatoethyl)-4-methyl-6-hydroxy-2-pyridone-3-sulfonic acid, 1-carboxymethyl-4-methyl-6-hydroxy-2-pyridone, 1-carboxymethyl-3-cyano-4-methyl-6-hydroxy-2-pyridone, 1-carboxymethyl-3-carbamoyl-4-methyl-6-hydroxy-2-pyridone, 1-carboxymeethyl-4-methyl-6-hydroxy-2-pyridone-3-sulfonic acid, 1-(β-carboxyethyl)-4-methyl-6-hydroxy-2-pyridone, 1-(β-carboxyethyl)-3-cyano-4-methyl-6-hydroxy-2-pyridone, 1-(β-carboxyechyl)-3-carbamoyl-4-methyl-6-hydroxy-2-pyridone, 1-(β-carboxyethyl)-4-methyl-6-hydroxy-2-pyridone-2-sulfonic acid, 1-(β-acetylaminoethyl)-4-methyl-6-hydroxy-2-pyridone, 1-(β-acetylaminoethyl)-3-cyano-4-methyl-6-hydroxy-2-pyridone, 1-(β-acetylaminoethyl)-3-carbamoyl-4-methyl-6-hydroxy-2-pyridone, 1-(β-acetylaminoethyl)-4-methyl-6-hydroxy-2-pyridone-3-sulfonic acid, 1-(β-acetylaminopropyl)-4-methyl-6-hydroxy-2-pyridone, 1-(β-acetylaminopropyl)-3-cyano-4-methyl-6-hydroxy-2-pyridone, 1-(β-acetylaminopropyl)-3-carbamoyl-4-methyl-6-hydroxy-2-pyridone, 1-(β-acetylaminopropyl)-4-methyl-6-hydroxy-2-pyridone-3-sulfonic acid, 4-hydroxy-2-quinoline, 1-amino- 8-hydroxy-2-(βphenylazo)naphthalene-3,6-disulfonic acid, 1-amino-8-hydroxy-2-(4'-sulfophenylazo)naphthalene-3,6-disulfonic acid, 1-amino-8-hydroxy-2-(2',5'-disulfophenylazo)naphthalene-3,6-disulfonic acid, 1-(β-aminoethyl)-3-cyano-4-methyl-6-hydroxy-2-pyridone, 1-(β-aminopropyl)-3-sulfomethyl-4-methyl-6-hydroxy-2-pyridone, 1,3-diaminobenzene, 1-amino-3-(N,N-di-β-hydroxyethylamino)benzene, 1-amino-3-(N,N-di-β-sulfatoethylamino)benzene, 1-amino-(3-N,N-di-β-hydroxyethylamino)-4-methoxybenzene, 1-amino-3-(N,N-di-β-sulfatoethylamino)-4-methoxybenzene, 1-amino-3-(sulfobenzylamino)benzene, 1-amino-3-(sulfobenzylamino)-4-chlorobenzene, 1-amino-3-(N,N-disulfobenzylamino)benzene, 1-hydroxy-3- or -4-methylbenzene, 1-hydroxybenzene-4-sulfonic acid, 1-hydroxynaphthalene, 2-hydroxynaphthalene, 2-hydroxynaphthalene-6- or -7-sulfonic acid, 1-hydroxynaphthalene-4,7-disulfonic acid, 1-amino-3-methylbenzene, 1-amino-2-methoxy-5-methylbenzene, 1-amino-2,5-dimethylbenzene, 3-aminophenylurea, 1-amino-3-acetylaminobenzene, 1-amino-3-(hydroxyacetylamino)benzene, 1,3-diaminobenzene-4-sulfonic acid, 1-aminonaphthalene-6- or -8-sulfonic acid, 1-amino-2-methoxynaphthalene-6-sulfonic acid, 2-aminonaphthalene-5,7-disulfonic acid, 1-amino-8-hydroxynaphthalene-6-sulfonic acid, 2-hydroxy-3-aminonaphthalene-5,7-disulfonic acid, 1-amino-8-hydroxynaphthalene-2,4,6-trisulfonic acid, 1-hydroxy-8-acetylaminonaphthalene-3-sulfonic acid, 1-benzoylamino-8-hydroxynaphthalene-3,6- or -4,6-disulfonic acid, 2-benzoylamino-5-hydroxynaphthalene-7-sulfonic acid, 2-methyl- and 2-ethylamino-5-hydroxynaphthalene-7-sulfonic acid, 2-(N-acetyl-N-methylamino)-5-hydroxynaphthalene-7-sulfonic acid, 2-ethylamino-8-hydroxynaphthalene-6-sulfonic acid, 2-acetylamino-8-hydroxynaphthalene-6-sulfonic acid, 1-(4'-aminobenzoylamino)-8-hydroxynaphthalene-3,6- and -4,6-disulfonic acid, 1-(4'-nitrobenzoylamino)-8-hydroxynaphthalene-3,6- and -4,6-disulfonic acid, 1-(3'-aminobenzoylamino)-6-hydroxynaphthalene-3,6- and -4,6-disulfonic acid, 1-(3'-nitrobenzoylamino)-8-hydroxynaphthalene-3,6- and -4,6-disulfonic acid, 2-(4'-amino-3'-sulfophenyl)amino-5-hydroxynaphthalene-7-sulfonic acid, 3-methyl-5-pyrazolone, 1-phenyl-3-methyl-5-pyrazolone, 1-(3'-aminophenyl)-3-methyl-5-pyrazolone, 1-(2',5'-disulfophenyl)-3-methyl-5-pyrazolone, 1-(2'-methyl-4'-sulfophenyl)-5-pyrazolone-3-carboxylic acid, 1-(4'8'-disulfonaphthyl-2'-yl)-3-methyl-5-pyrazolone, 1-(5'7'-disulfonaphthyl-2-)-3-methyl-5-pyrazolone, 1-(2'5'-dichloro-4'-sulfophenyl)-3-methyl-5-pyrazolone, 3-aminocarbonyl-4-methyl-6-hydroxy-2-pyridone, 1-ethyl-3-cyano- or -3-chloro-4-methyl-6-hydroxy-2-pyridone, 1-ethyl-3-sulfomethyl-4-methyl-6-hydroxy-2-pyridone, 2,4, 6-triamino-3-cyanopyridine, 2-(3'-sulfophenyl)amino-4,6-diamino-3-cyanopyridine, 2-(2'-hydroxyethylamino)-3-cyano-4-methyl-6-aminopyridine, 2,6-bis-(2'-hydroxyethylamino)-3-cyano-4-methylpyridine, 1-ethyl-3-carbamoyl-4-methyl-6-hydroxy-2-pyridone, 1-ethyl-3-sulfomethyl-4-methyl-5-carbamoyl-6-hydroxy-2-pyridone, N-acetoacetylaminobenzene, 5-acetylamino-2-sulfoaniline.

The comdounds of the general formula (5) usable according to the invention for the synthesis of the azo compounds (1) according to the invention are hitherto unknown. The invention accordingly also relates to these compounds, processes for their preparation and their use for the synthesis of dyes, such as, in particular, of the azo compounds (1) according to the invention.

The compounds of the general formula (5) may be prepared according to the invention by reacting a compound of the general formula (6)

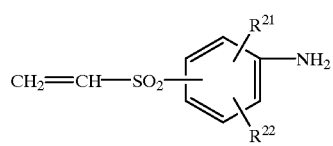

(6)

where $R^{21}$ and $R^{22}$ are each as defined above, in an aqueous medium at a pH of 10 to 12 and a temperature of 10 to 30° C. with an amino compound of the general formula (7)

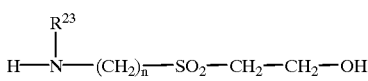

(7)

where $R^{23}$ and n are each as defined above, and optionally converting the β-hydroxyethyl group in the resulting compound of the general formula (5) where $Y^1$ is β-hydroxyethyl in a conventional manner into a group $Y^1$ having a meaning other than β-hydroxyethyl, for example into their ester derivatives, such as, for example, of polybasic inorganic acids or of aliphatic and aromatic carboxylic or sulfon c acids, for example into compounds in which yl is β-chloroethyl, β-sulfatoethyl, β-phosphatoethyl, β-thiosulfatoethyl, β-acetyloxyethyl or β-toluylsulfonyloxyethyl. Examples of suitable esterification and acylating agents are the corresponding inorganic or organic acids or their anhydrides or halides or amides, such as, for example, sulfuric acid, sulfuric acid containing sulfur trioxide, chlorosulfonic acid, sulfamic acid, phosphoric acid, phosphorus oxychloride, mixtures of phosphoric acid and phosphorus pentoxide, acetic anhydride, toluenesulfonyl chloride and thionyl chloride.

Those compounds of the general formulae (1) and (5) in which Y and $Y^1$ are the vinyl group can be prepared from their analogous ester derivatives by means of alkali, for example in aqueous medium at a pH of 10 to 12 and a temperature between 20 and 50° C. and a reaction time of 10 to 20 minutes. The synthesis of, for example, β-(dialkylamino)ethylsulfonyl and β-thiosulfatoethylsulfonyl derivatives of the compounds (1) and (5) is carried out by reaction of their vinylsulfonyl compounds with the corresponding dialkylamine or with an alkali metal salt of thiosulfuric acid, such as sodium hiosulfate. All these procedures of converting one group $-SO_2-Y$ or $-SO_7-Y$ into another are known to one skilled in this field of fiber-reactive dyes and are described in the literature in large numbers.

The compounds according to the invention of the general formula (1)—hereinafter designated as compounds (1)—have fiber-reactive properties and have very valuable dye properties. They can therefore be used for the dyeing (including printing) of hydroxy-containing and/or carboxamido-containing materials. For this purpose, the solutions formed in the synthesis of the compounds (1), if desired after the addition of a buffer substance and if also desired after concentration, can be used directly as liquid preparation for dyeing.

The compounds (1) can be precipitated and isolated from the aqueous synthesis solutions by generally known methods for water-soluble compounds, for example by precipitation from the reaction medium by means of an electrolyte, such as, for example, sodium chloride or potassium chloride, or, alternatively, by evaporation of the reaction solution itself, for example by spray-drying. If the last-mentioned type of isolation is chosen, it is in many cases advisable to remove any amounts of sulfate present in the solutions, before the evaporation, by precipitation as calcium sulfate and separation by filtration.

The present invention accordingly also relates to the use or the compounds (1) for the dyeing (including printing) of hydroxy- and/or carboxamido-containing materials and to processes for applying them to these substrates. The materials are preferably used in the form of fiber materials, in particular in the form of textile fibers, such as yarns, wound articles and fabrics. This is done analogously to known procedures.

Hydroxy-containing materials are those of natural or synthetic origin, such as, for example, cellulose fiber materials or their regenerated products and polyvinyl alcohols. Cellulose fiber materials are preferably cotton, but also other vegetable fibers, such as linen, hemp, jute and ramie fibers; examples of regenerated cellulose fibers are staple viscose and filament viscose.

Examples of carboxamido-containing materials are synthetic and natural polyamides and polyure-Lhanes, in particular in the form of fibers, for example wool and other animal hair, silk, leather, nylon-6,6, nylon-6, nylon-11 and nylon-4.

The compounds (1) can be applied and fixed, in accordance with the use according to the invention, on the substrates mentioned, in particular on the fiber materials mentioned, by the application techniques known for water-soluble, fiber-reactive dyes, for example by applying the compound (1) in dissolved form to the substrate or incorporating it therein and fixing it on it or in it, if necessary by applying heat and/or if necessary by applying an alkaline agent. These dyeing and fixation procedures have been described in the literature in large numbers (see, for example, European Patent Application Publication No. 0,181,585 A2).

The dyeings according to the invention have good light fastness properties, in particular on cellulose fiber materials, not only in dry conditions but also in wet conditions, for example moistened with a perspiration solution, and also good wet fastness properties, such as, for example, good wash fastness at 60 to 95° C., also in the presence of perborates, good acid and alkaline milling, cross-dyeing and perspiration fastness properties, high resistance to steam, good alkali, acid, water and sea water fastness, furthermore good pleating fastness, hot press fastness and rub fastness. Likewise they have good acid fading resistance upon storage of moist dyed material still containing acetic acid.

The Examples which follow serve to illustrate the invention. Parts and percentages are by weight, unless stated otherwise. Parts by weight relate to parts by volume as the kilogram relates to the liter.

The compounds described in these Examples by way of their formulae are given in the form of the free acids; in general, they are prepared and isolated in the form of their alkali metal salts, such as lithium salts, sodium salts or potassium salts, and used for dyeing in the form of their salts. Likewise, the starting compounds and components mentioned in the Examples below, in particular the Table Examples, in the form of the free acid, can be use: in the synthesis as such or in the form of their salts, preferably alkali metal salts.

The absorption maxima ($\lambda_{max}$) given for the compounds according to the invention in the visible region were determined using their alkali metal salts in aqueous solution. In the Table Examples, the $\lambda_{max}$ values are written in parentheses next to the hue; the wavelengths are given in nm.

EXAMPLE A

In a pH of 6.5 solution of 281 parts of 4-(β-sulfatoethylsulfonyl)-aniline in about 1000 parts of water, this aniline compound is converted into its vinylsulfonyl compound in a conventional manner by means of 2N sodium hydroxide solution at a temperature from 15 to 20° C. with stirring; the batch is subsequently admixed at pH 8.5 with a solution of 167 parts of N-methyl-N-[β-(β'-hydroxyethylsulfonyl)-ethyl]-amine in 600 parts of water. The batch is further stirred for some hours at a pH maintained at 8, and the precipitated product is filtered off with suction, washed with about 100 parts of ice-water and dried at 50° C. under reduced pressure.

The resulting compound of the formula

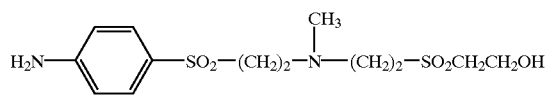

melts at 82–85° C. and exhibits the following bands in the IR spectrum: 3450 cm$^{-1}$ (NH), 3380 cm$^{-1}$ (NH), 2920 cm$^{-1}$ (CH), 1660 cm$^{-1}$ (CH), 1595 cm$^{-1}$ (CH).

EXAMPLE 1

35 parts of the aniline compound of Example A are introduced at 40° C. into 80 parts of sulfuric acid monohydrate; the batch is further stirred at that temperature for some hours and then poured onto 1000 parts of ice. A conventional diazotization is carried out by adding about 20 parts of aqueous 5N sodium nitrite solution, excess nitrite is removed with amidosulfonic acid, 38.1 parts 4,6-disulfo-1-benzoylamino-8-naphthol are added to this diazonium salt solution at 5° C., a pH of 5.5 is set, and the batch is warmed to 15 to 20° C. and stirred for a while longer.

The azo compound of the invention, which in the form of the free acid conforms to the formula

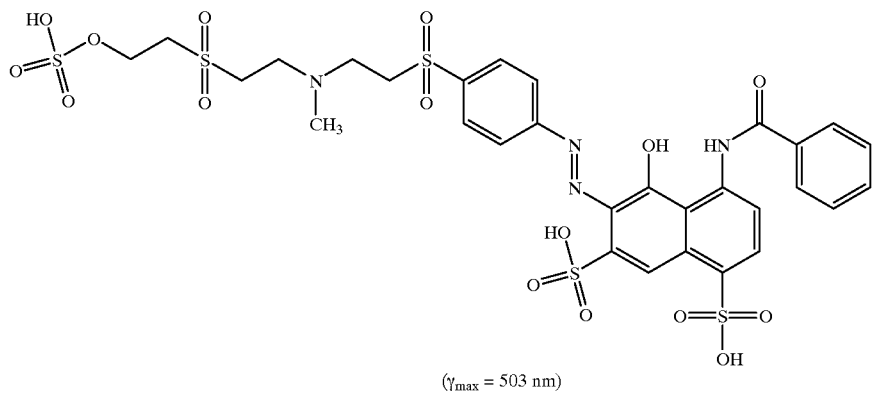

($\gamma_{max}$ = 503 nm)

is isolated by salting out, for example with sodium chloride, as its alkali metal salt (sodium salt). It has very good fiber-reactive dye properties and provides on the materials mentioned in the description part, especially cellulose fiber materials, for example cotton, by the application and fixing methods known for fiber-reactive dyes strong red dyeings and prints which are notable in particular for their good washoff properties.

EXAMPLE 2

Example 1 is repeated to diazotize 70 parts of the aniline compound of Example A, and half this diazonium salt solution is gradually and continuously added at 5° C. to a neutral solution of 17.6 parts of 3-amino-4-sulfoaniline in 1000 parts of water; the pH changes to 2.5 in the course of the reaction and is maintained by means of sodium carbonate. The batch is then warmed to 10 to 15° C., stirred for some while longer, the monoazo compound of the invention is isolated by suction filtration, and it is converted into the disazo compound according to the invention of the formula (written in the form of the free acid)

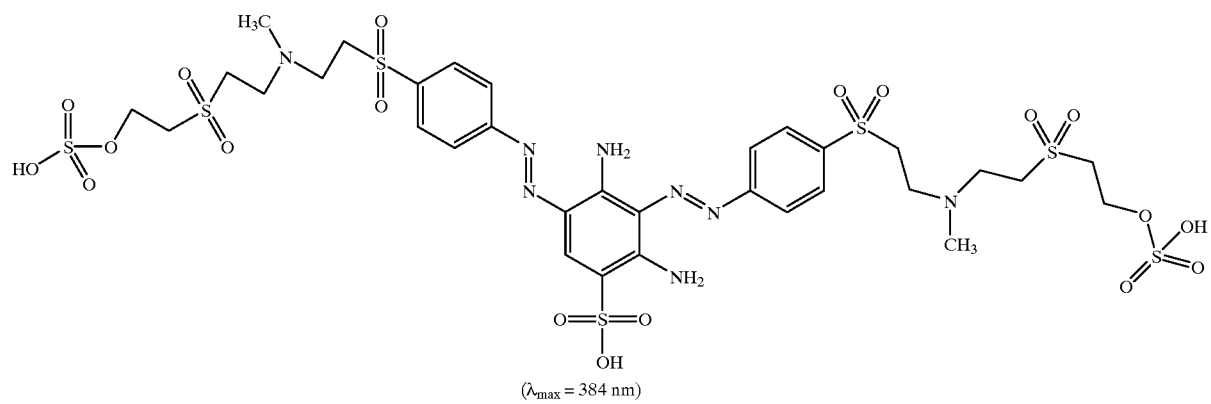

($\lambda_{max}$ = 384 nm)

by suspending it in 1000 parts of water and admixing it with the second half of the diazonium salt solution at a pH of 5 to 6 and a temperature of 15 to 20° C. Stirring is continued under these reaction conditions and the disazo compound of the invention is isolated in a conventional manner as alkali metal salt. It has very good fiber-reactive dye properties and provides for example on cellulose fiber materials, such as cotton, by the known application techniques strong golden yellow dyeings and prints which are notable in particular for their good washoff properties.

EXAMPLES 3 to 33

The Table Examples which follow describe further azo compounds according to the invention, conforming (when written. in the form of the free acid) to the general formula (A)

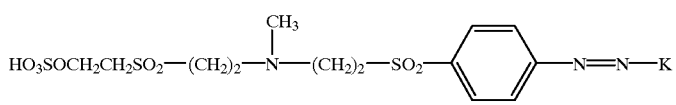

(A)

by means of the formula radical K. They can be prepared by the procedure according to the invention, for example analogously to one of the above Working Examples, and likewise have very good fiber-reactive dye properties. They produce dyeings and prints of high color strength on the materials mentioned in the description, such as, in particular, cellulose fiber materials, by the application and fixation methods customary for fiber-reactive dyes in the hue given in the particular table example (in this case on cotton) which have good fastness properties.

| Ex. | Radical -K | Hue |
| --- | --- | --- |
| 3 | 1,5-Diamino-4-sulfo-2-[4'-(β'-sulfatoethyl-sulfonyl)phenyl]azo-phen-6-yl | golden yellow (384) |
| 4 | (1-(4'-β-Sulfatoethylsulfonylphenyl)-3-methyl-5-one-pyrazol-4-yl | yellow (416) |
| 5 | 1-(4'-Sulfophenyl)-3-methyl-5-one-pyrazol-4-yl | yellow (413) |
| 6 | 1-(2'-Chloro-5'-sulfophenyl)-3-methyl-5-one-pyrazol-4-yl | yellow (414) |
| 7 | 1-(4'-Sulfophenyl)-3-carboxy-5-one-pyrazol-4-yl | yellow (415) |
| 8 | 1-(4'-Sulfophenyl)-3-carbethoxy-5-one-pyrazol-4-yl | yellow (414) |
| 9 | 1-(N-β-Sulfoethyl)-4-methyl-2-hydroxy-6-one-pyrid-3-yl | yellow (423) |
| 10 | 5-Sulfo-1,4-dimethyl-2-hydroxy-6-one-pyrid-3-yl | yellow (420) |
| 11 | 2-Oxo-3-(2'-carboxyphenylamino)carbonyl-prop-3-yl | yellow |
| 12 | 2-Oxo-3-(3'-sulfophenylamino)carbonyl-prop-3-yl | yellow |
| 13 | 2-Oxo-3-(2'-methoxy-5'-methyl-4'-sulfo-phenylamino)carbonyl-prop-3-yl | yellow (401) |
| 14 | 1-Amino-5-acetylamino-2-sulfo-phen-4-yl | yellow (407) |
| 15 | 1-[N,N-Bis-(β-sulfatoethyl)]amino-phen-4-yl | orange (448) |
| 16 | 1-[N,N-Bis-(β-sulfatoethyl)]amino-3-chloro-phen-4-yl | orange (452) |
| 17 | 1-[N-Ethyl-N-(β-sulfatoethyl)]amino-phen-4-yl | red |
| 18 | 4-Sulfo-1-naphth-2-yl | red |
| 19 | 3,6-Disulfo-2-naphth-1-yl | red |

-continued

| Ex. | Radical -K | Hue |
| --- | --- | --- |
| 20 | 6-Sulfo-3-acetylamino-8-hydroxynaphth-7-yl | orange (475) |
| 21 | 6-Sulfo-2-acetylamino-8-hydroxynaphth-7-yl | red (509) |
| 22 | 4,6-Disulfo-3-(4'-fluoro-6'-morpholino-1', 3',5'-triazin-2'-yl)amino-8-hydroxynaphth-7-yl | orange (470) |
| 23 | 4,6-Disulfo-1-acetylamion-8-hydroxynaphth-7-yl | bluish red (505) |
| 24 | 3,6-Disulfo-1-benzoylamino-8-hydroxynaphth-7-yl | bluish red (509) |

-continued

| Ex. | Radical -K | Hue |
| --- | --- | --- |
| 25 | 3,6-Disulfo-1-acetylamino-8-hydroxynaphth-7-yl | bluish red |
| 26 | 3,6,8-Trisulfo-1-hydroxynaphth-2-yl | bluish red |
| 27 | 6-Sulfo-2-benzoylamino-8-hydroxynaphth-7-yl | red |
| 28 | 3,6-Disulfo-1-[4'-chloro-6'-(3"-sulfo-phenyl)amino-1',3',5'-triazin-2'-yl]amino-8-hydroxynaphth-7-yl | bluish red (516) |
| 29 | 3,6-Disulfo-1-{4'-chloro-6'-[4"-(β-sulfato-ethylsulfonyl)phenyl]amino-1',3',5'-triazin-2'-yl}amino-8-hydroxynaphth-7-yl | bluish red (521) |
| 30 | 3,6-Disulfo-1-(4'-fluoro-6'-[4"-(β-sulfato-ethylsulfonyl)phenyl]amino-1',3',5'-triazin-2'-yl]amino-8-hydroxynaphth-7-yl | bluish red (522) |
| 31 | 3,6-Disulfo-1-[4'-fluoro-6'-morpholino-1',3',5'-triazin-2'-yl]amino-8-hydroxy-naphth-7-yl | bluish red (519) |
| 32 | 3,6-Disulfo-1-amino-2-[4'-(β-sulfatoethyl-sulfonyl)phenyl]-azo-8-hydroxynaphth-7-yl | navy (625) |
| 33 | 3,6-Disulfo-1-amino-2-[2'-methoxy-5'-(β-sulfatoethylsulfonyl)phenyl]-azo-8-hydroxynaphth-7-yl | navy (628) |

EXAMPLES 34 to 65

The Table Examples which follow describe further azo compounds cording to the invention, conforming (when written in the rm of the free acid) to the general formula (B)

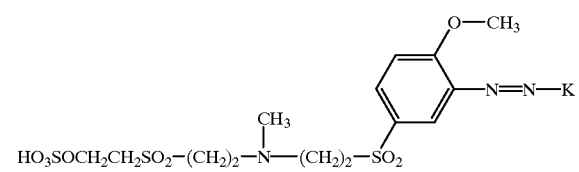

(B)

by means of the formula radical K. They can be prepared by the prooocedure according to the invention, for example analogously to one of the above exemplary embodiments, and have very good fiber-reactive dye properties. They produce dyeings and prints of high color strength on the materials mentioned in the discription, such as, in particular, cellulose fiber materials, by the application and fixation methods customary for fiber-reactive dyes in the hue given in the particular table example (in this case on cotton) which have good fastness properties.

| Ex. | Radical -K | Hue |
|---|---|---|
| 34 | 1,5-Diamino-4-sulfo-2-[4'-(β'-sulfatoethylsulfonyl)phenyl]azo-phen-6-yl | golden yellow (387) |
| 35 | 1-(4'-β-Sulfatoethylsulfonylphenyl)-3-methyl-5-one-pyrazol-4-yl | yellow (418) |
| 36 | 1-(4'-Sulfophenyl)-3-methyl-5-one-pyrazol-4-yl | yellow |
| 37 | 1-(2'-Chloro-5'-sulfophenyl)-3-methyl-5-one-pyrazol-4-yl | yellow |
| 38 | 1-(4'-Sulfophenyl)-3-methyl-5-one-pyrazol-4-yl | yellow |
| 39 | 1-(4'-Sulfophenyl)-3-carbethoxy-5-one-pyrazol-4-yl | yellow (417) |
| 40 | 1-(N-β-Sulfoethyl)-4-methyl-2-hydroxy-6-one-pyrid-3-yl | yellow (425) |
| 41 | 5-Sulfo-1,4-dimethyl-2-hydroxy-6-one-pyrid-3-yl | yellow |
| 42 | 2-Oxo-3-(2'-carboxyphenylamino)carbonyl-prop-3-yl | yellow |
| 43 | 2-Oxo-3-(3'-sulfophenylamino)carbonyl-prop-3-yl | yellow |
| 44 | 2-Oxo-3-(2'-methoxy-5'methyl-4'-sulfophenyl-amino)carbonyl-prop-3-yl | yellow (404) |
| 45 | 1-Amino-5-acetylamino-2-sulfo-phen-4-yl | yellow |
| 46 | 1-[N,N-Bis-(β-sulfatoethyl)]amino-phen-4-yl | orange (450) |
| 47 | 1-[N,N-Bis-(β0sulfatoethyl)]amino-3-chloro-phen-4-yl | orange |
| 48 | 1-[N-Ethyl-N-(β0sulfatoethyl)]amino-phen-4-yl | red |
| 49 | 4-Sulfo-1-hydroxynaphth-2-yl | red |
| 50 | 3,5-Disulfo-2-hydroxynaphth-2-yl | red |
| 51 | 6-Sulfo-3-acetylamino-8-hydroxynaphth-7-yl | orange (478) |
| 52 | 6-Sulfo-2-acetylamino-8-hydroxynaphth-7-yl | red |
| 53 | 4,5-Disulfo-3-(4'-fluoro-6'-morpholino-1',3',5'-triazin-2'-yl)amino-8-hydroxynaphth-7-yl | orange (474) |
| 54 | 4,5-Disulfo-1-acetylamino-8-hydroxynaphth-7-yl | bluish red (508) |
| 55 | 4,5-Disulfo-1-benzoylamino-8-hydroxynaphth-7-yl | bluish red (510) |
| 56 | 3,5-Disulfo-1-benzoylamino-8-hydroxynaphth-7-yl | bluish red (512) |
| 57 | 3,5-Disulfo-1-acetylamino-8-hydroxynaphth-7-yl | bluish red |
| 58 | 3,5,8-Trisulfo-1-hydroxynaphth-2-yl | bluish red |
| 59 | 6-Sulfo-2-benzoylamino-8-hydroxynaphth-7-yl | red |
| 60 | 3,5-Disulfo-1-[4'-chloro-6'-(3"sulfophenyl)-amino-1',3',5'-triazin-2'yl]amino-8-hydroxy-naphth-7-yl | bluish red (517) |
| 61 | 3,5-Disulfo-1-{4'-chloro-6'-[4"-(β-sulfatoethylsulfonyl)phenyl]amino-1',3',5'-triazin-2'-yl}amino-8-hydroxynaphth-7-yl | bluish red (523) |
| 62 | 3,5-Disulfo-1-{4'-fluoro-6'-[4"-(β-sulfatoethylsulfonyl)phenyl]amino-1',3',5'-triazin-2'-yl}amino-8-hydroxynaphth-7-yl | bluish red (524) |
| 63 | 3,5-Disulfo-1-[4'-fluoro-6'-morpholin-1',3',5'-triazin-2'yl]amino-8-hydroxynaphth-7-yl | bluish red (522) |
| 64 | 3,5-Disulfo-1-amino-2-[4'-(β-sulfatoethyl-sulfonyl)phenyl]azo-8-hydroxynaphth-7-yl | navy (628) |
| 65 | 3,5-Disulfo-1-amino-2-[2'-methoxy-5'-(β-sulfatoethylsulfonyl)phenyl]azo-8-hydroxynaphth-7-yl | navy (631) |

What is claimed is:
1. An azo compound of the general formula (1)

D–N=N–K (1)

in which:
D is a group of the general formula (2)

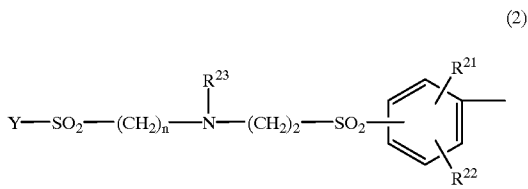

(2)

in which:
R$^{21}$ is hydrogen, methyl, ethyl, methoxy, ethoxy or sulfo;
R$^{22}$ is hydrogen, methyl, ethyl, methoxy, ethoxy or sulfo;
R$^{23}$ is hydrogen, alkyl of 1 to 4 carbon atoms or phenyl;
n is 2 or 3;
Y is vinyl or is a group of the general formula (3)

—CH$_2$—CH$_2$—Z (3)

where Z is a substituent which is eliminable by alkali with the formation of a vinyl group;
K is the radical of a sulfo- or carboxy- or sulfo- and carboxy-containing compound which possesses the function of a singly or doubly coupleable coupling component or contains the latter as a moiety attached to the azo group, the coupling component being selected from the following compounds: aminobenzenes, diaminobenzenes and phenols; naphthols; aminonaphthols; acylaminonaphthols with the acyl radical of an alkanecarboxylic acid having 1 to 4 carbon atoms in the alkyl group, or of an alkenecarboxylic acid having 2 to 4 carbon atoms in the alkenyl group, or of an aromatic carboxylic acid, of an aromatic sulfonic acid or of an N-substituted carbamic acid; dihydroxynaphthalenesulfonic acids; phenylazo- and naphthylazoaminonaphtholsulfonic acids; 5-pyrazolones and 5-aminopyrazoles; acetoacetylarylides; 2-hydroxy-6-pyridones; hydroxyquinolines; the radical K optionally containing one or more fiber-reactive groups in addition to substituents that are in water-soluble dyes.
2. An azo compound as claimed in claim 1, wherein K contains a fiber-reactive group of the general formula —SO$_2$Y where Y is as defined in claim 1, or a 2-chloro- or 2-fluoro-4-morpholino-1,3,5-triazin-6-ylamino group or a 2-fluoro- or 2-chloro-4-amino-1,3,5-triazin-6-ylamino group whose 4-disposed amino group may be mono- or disubstituted by substituents selected from alkyl of 1 to 4 carbon atoms, phenyl and phenyl substituted by substituents selected from the group consisting of sulfo, carboxy, methyl, ethyl, methoxy, ethoxy, chlorine, bromine and —SO$_2$—Y where Y is as defined in claim 1.
3. An azo compound as claimed in claim 1, wherein K contains a fiber-reactive group of the general formula —SO$_2$Y where Y is as defined in claim 1.
4. An azo compound as claimed in claim 1, wherein K contains no fiber-reactive group.
5. An azo compound as claimed in claim 1, wherein Y is vinyl or β-sulfatoethyl.
6. An azo compound as claimed in claim 1, wherein n is 2.
7. An azo compound as claimed in claim 1, wherein R$^{23}$ is alkyl of 1 to 4 carbon atoms.
8. An azo compound as claimed in claim 1, wherein R$^{21}$ and R$^{22}$ are both hydrogen.

9. An azo compound as claimed in claim 1, wherein the SO$_2$ grouping in D is para to the azo group.

10. An azo compound as claimed in claim 1, wherein K is the radical of a sulfo- or carboxy- or sulfo- and carboxy-containing compound which possesses the function of a singly or doubly coupleable coupling component or contains the latter as a moiety attached to the azo group, the coupling component being selected from the following compounds: aminobenzenes sulfonic acids and carboxylic acids, diaminobenzenes sulfonic acids and carboxylic acids and phenols sulfonic acids and carboxylic acids; naphthols sulfonic acids and carboxylic acids; aminonaphthols sulfonic acids; acylaminonaphthols sulfonic acids with the acyl radical of an alkanecarboxylic acid having 1 to 4 carbon atoms in the alkyl group or of an alkenecarboxylic acid having 2 to 4 carbon atoms in the alkyl group or of an aromatic carboxylic acid or of an aromatic sulfonic acid or of an N-substituted carbamic acid; dihydroxynaphthalenesulfonic acids; phenylazo- and naphthylazoaminonaphtholsulfonic acids; 5-pyrazolones and 5-aminopyrazoles; acetoacetylarylides; 2-hydroxy-6-pyridones; hydroxyquinolines; the radical K optionally containing one or more fiber-reactive groups in addition to the substituents that are in water-soluble dyes.

11. A process for preparing the azo compound of the general formula (1) as claimed in claim 1, which comprises reacting a diazonium compound of an amino compound of the general formula (5)

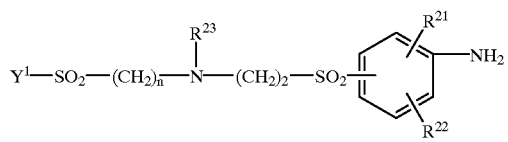
(5)

where R$^{21}$, R$^{22}$, R$^{23}$ and n are as defined in claim 1, Y$^1$ is β-hydroxyethyl or is vinyl or a group of the formula (3) as defined in claim 1, with a compound of the general formula H—K where K is as defined in claim 1 and when Y$^1$ is β-hydroxyethyl, converting this group into a group Y.

12. A process as claimed in claim 11, wherein a further azo group is introduced into K by coupling reaction with a diazonium compound or where a fiber-reactive group of the formula (a), (b) or (c)

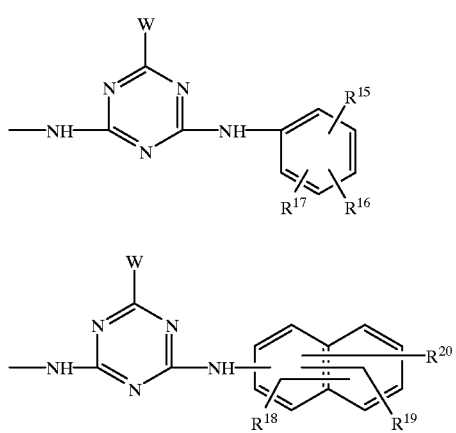
(a)

(b)

(c)

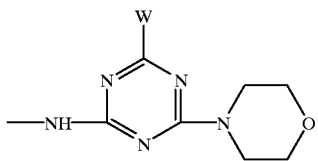

where
R$^{15}$ is hydrogen, sulfo, carboxy or a group of the general formula —SO$_2$—Y where Y is vinyl or a group of the formula (3)

—CH$_2$—CH$_2$—Z   (3)

where Z is a substituent eliminable by alkali with the formation,

R$^{16}$ is hydrogen, alkyl of 1 to 4 carbon atoms, alkoxy of 1 to 4 carbon atoms, chlorine, bromine, carboxy, sulfo or nitro, R$^{17}$ is hydrogen, alkyl of 1 to 4 carbon atoms, alkoxy of 1 to 4 carbon atoms, chlorine or bromine, R$^{18}$ is hydrogen, sulfo, carboxy or a group of the general formula —SO$_2$—Y where Y is as defined above, R$^{19}$ is hydrogen or sulfo, R$^{20}$ is hydrogen or sulfo, and W is fluorine or chlorine, is introduced into K.

13. The process as claimed in claim 12, wherein
R$^{16}$ is hydrogen, methoxy, ethoxy, methyl, ethyl, sulfo or carboxy, R$^{17}$ is hydrogen, methoxy or ethoxy, and R$^{18}$ is hydrogen, sulfo or a group of the formula —SO$_2$Y.

14. A process for dyeing hydroxy- and/or carboxamido-containing material which comprises applying a dye to the material and fixing the dye on the material by
(a) means of heat,
(b) with the aid of an alkaline agent or
(c) by means of heat and with the aid of an alkaline agent.

15. The process as claimed in claim 14, wherein said material is a fiber material.

16. A compound of the general formula (5)

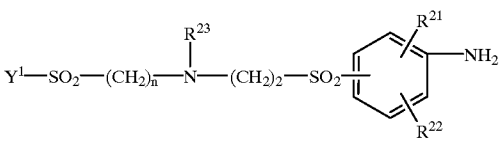
(5)

where
R$^{21}$ is hydrogen, methyl, ethyl, methoxy, ethoxy or sulfo;
R$^{22}$ is hydrogen, methyl, ethyl, methoxy, ethoxy or sulfo;
R$^{23}$ is hydrogen, alkyl of 1 to 4 carbon atoms or phenyl;
n is 2 or 3;
Y$^1$ is vinyl or is a group of the general formula (3)

—CH$_2$—CH$_2$—Z   (3)

where Z is a substituent which is eliminable by alkali with the formation of a vinyl group, or is β-hydroxyethyl.

17. A compound as claimed in claim 16, wherein Y$^1$ is vinyl or β-sulfatoethyl.

18. A compound as claimed in claim 16, wherein n is 2.

19. A compound as claimed in claim 16, wherein $R^{23}$ is alkyl of 1 to 4 carbon atoms.

20. A compound as claimed in claim 16, wherein $R^{21}$ and $R^{22}$ are both hydrogen.

21. A compound as claimed in claim 16, wherein the $SO_2$ grouping is para to the amino group.

22. A process for preparing a compound of the general formula (5) mentioned and defined in claim 16, which comprises reacting a compound of the general formula (6)

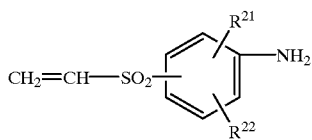
(6)

where $R^{21}$ and $R^{22}$ are each as defined in claim 16, in an aqueous medium at a pH of 10 to 12 and a temperature of 10 to 30° C. with an amino compound of the general formula (7)

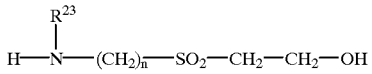
(7)

where $R^{23}$ and n are each as defined in claim 16, and optionally converting the β-hydroxyethyl group in the resulting compound of the general formula (5) where $Y^1$ is β-hydroxyethyl, into a group $Y^1$ having a meaning other than β-hydroxyethyl.

* * * * *